United States Patent [19]

Sugimori et al.

[11] 4,422,951

[45] Dec. 27, 1983

[54] LIQUID CRYSTAL BENZENE DERIVATIVES

[75] Inventors: Shigeru Sugimori, Fujisawashi; Tetsukiko Kojima; Masakazu Tsuji, both of Yokohamashi, all of Japan

[73] Assignee: Chisso Corporation, Osaka, Japan

[21] Appl. No.: 358,794

[22] Filed: Mar. 16, 1982

[30] Foreign Application Priority Data

| Apr. 2, 1981 | [JP] | Japan | 56-49688 |
| Apr. 2, 1981 | [JP] | Japan | 56-49689 |
| Aug. 18, 1981 | [JP] | Japan | 56-129070 |
| Sep. 3, 1981 | [JP] | Japan | 56-138875 |
| Oct. 27, 1981 | [JP] | Japan | 56-171696 |

[51] Int. Cl.³ .......... G02F 1/13; C09K 3/34; C07C 43/21; C07C 13/28
[52] U.S. Cl. .......... 252/299.63; 252/299.5; 252/299.6; 568/631; 585/20; 585/23; 585/25; 350/350 R
[58] Field of Search ............ 252/299.63, 299.6, 299.5; 585/20, 23, 25; 568/631; 350/350

[56] References Cited

U.S. PATENT DOCUMENTS

| 4,154,697 | 5/1979 | Eidenschink et al. | 252/299.63 |
| 4,181,625 | 1/1980 | Eidenschink et al. | 252/299.63 |
| 4,198,130 | 4/1980 | Boller et al. | 252/299.5 |
| 4,229,015 | 10/1980 | Krause et al. | 252/299.63 |
| 4,330,426 | 5/1982 | Eidenschink et al. | 252/299.63 |
| 4,331,552 | 5/1982 | Eidenschink et al. | 252/299.63 |
| 4,368,135 | 1/1983 | Osman | 252/299.63 |
| 4,386,007 | 5/1983 | Krause et al. | 252/299.62 |

FOREIGN PATENT DOCUMENTS

| 51738 | 5/1982 | European Pat. Off. | 252/299.63 |
| 2949080 | 6/1981 | Fed. Rep. of Germany | 252/299.62 |
| 3139130 | 5/1982 | Fed. Rep. of Germany | 252/299.63 |
| 56-68636 | 6/1981 | Japan | 252/299.6 |
| 2077286 | 12/1981 | United Kingdom | 252/299.63 |
| 2078727 | 1/1982 | United Kingdom | 252/299.6 |
| 2090593 | 7/1982 | United Kingdom | 252/299.62 |

OTHER PUBLICATIONS

Billard, J. et al., Mol. Cryst. Liq. Cryst., vol. 41 (Letters), pp. 217–222 (1978).
Karamysheva, L. A. et al., *Advances in Liq. Cryst. Res. and Appl.*, Bata, L., Percamon Press, Oxford, pp. 997–1002 (1980).
C.A., vol. 70, 46905x (1969).
C.A., vol. 68, 9160p (1968).

*Primary Examiner*—Teddy S. Gron
*Attorney, Agent, or Firm*—Wenderoth, Lind & Ponack

[57] ABSTRACT

Benzene derivatives useful as a component of liquid crystal compositions are provided which are expressed by the general formula

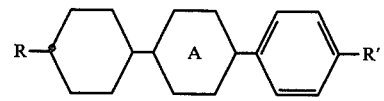

wherein R represents a hydrogen atom or an alkyl group of 1 to 10 carbon atoms; R' represents a hydrogen atom, an alkyl group of 1 to 10 carbon atoms or an alkoxy group of 1 to 10 carbon atoms; and

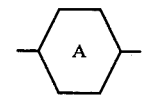

represents

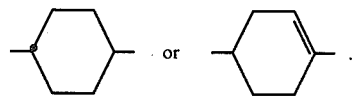

The derivatives exhibit small values of positive dielectric anisotropy; have broader liquid crystal temperature ranges; and in particular, have higher liquid crystalline-transparent points and yet have lower viscosities.

5 Claims, No Drawings

LIQUID CRYSTAL BENZENE DERIVATIVES

BACKGROUND OF THE INVENTION

This invention relates to novel liquid crystal substances which exhibit a liquid crystal phase within broad temperature ranges and have lower viscosities.

Liquid crystal display elements utilize optical anisotropy and dielectric anisotropy of liquid crystal substances, and are classified into various types such as TN type (twisted nematic type), DS type (dynamic scattering type), guest-host type, DAP type, etc. according to their display modes, and the properties of liquid crystal substances suitable to their respective uses are different. However, it is common to any liquid crystals that stabilities to moisture, air, heat, light, etc. are required, and it is also necessary that they exhibit a liquid crystal phase within as broad a temperature range as possible, around room temperature, and further, have an optimal value of dielectric anisotropy ($\Delta\epsilon$) varied depending on the kinds of display elements. At present, however, no single compound which alone satisfies such conditions is present, and it is the present status that a liquid crystal composition obtained by blending several kinds of liquid crystal compounds or non-liquid-crystal compounds is used. Recently, display elements actuating over from lower temperatures (about $-20°$ C.) up to higher temperatures (about 80°–90° C.) have been particularly needed; thus, liquid crystal compositions having superior actuation characteristics within a broader temperature range have been desired.

The object of the present invention is to provide novel liquid crystal compounds which are useful as a component of such liquid crystal compositions and particularly suitable to improvement in low temperature characteristics.

SUMMARY OF THE INVENTION

The present invention is directed to benzene derivatives expressed by the general formula

wherein R represents a hydrogen atom or an alkyl group of 1 to 10 carbon atoms; R' represents a hydrogen atom, an alkyl group of 1 to 10 carbon atoms or an alkoxy group of 1 to 10 carbon atoms; and

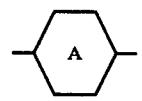

represents

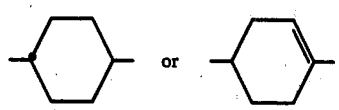

DETAILED DESCRIPTION OF THE INVENTION

The compounds of the present invention exhibit small values of positive dielectric anisotropy; have broader liquid crystal temperature ranges; and in particular, have higher liquid crystalline-transparent points (N-I points or Sm-I points) and yet have lower viscosities. Among the compounds of the formula (I), those wherein the group

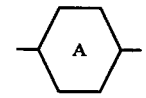

of formula (I) is

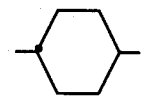

are particularly stable to heat, air, moisture, light, etc.; hence they are extremely useful for preparing liquid crystal compositions actuating within a broad temperature range over from lower temperatures up to higher ones.

Next, a process for preparing compounds of the present invention will be illustrated below.

Bromobenzene (in the case where R=H) or a 4-substituted-bromobenzene (in the case where R is other than H) is first reacted with metallic magnesium in tetrahydrofuran to give a 4-substituted-(or unsubstituted-)phenylmagnesium bromide (terms "or unsubstituted" will be omitted below), which is then reacted with 4-cyclohexylcyclohexanone (in the case where R=H) or a 4-(trans-4'-alkylcyclohexyl) cyclohexanone (in the case where R is other than H) (these cyclohexanones being obtained by oxidizing the corresponding cyclohexanols with anhydrous chromic acid), to give a 4-substituted-[1'-hydroxy-4'-(trans-4''-alkylcyclohexyl) cyclohexyl]benzene, which is then dehydrated in the presence of potassium hydrogen sulfate as catalyst, to give a 4-substituted-[4'-(trans-4''-alkylcyclohexyl)cyclohexen-1'-yl]benzene as one of the objective compounds. This compound is further reduced in ethanol as solvent in the presence of Raney nickel catalyst under the atmospheric pressure and at 30° C. to give a 4-substituted-[4'-(trans-4''-alkylcyclohexyl)cyclohexyl]benzene. Since this compound is a mixture of trans-form with cis-form, it is recrystallized from ethanol to give an objective 4-substituted-[trans-4'-(trans-4''-alkylcyclohexyl) cyclohexyl]benzene. The above reactions can be illustrated by chemical equations as follows:

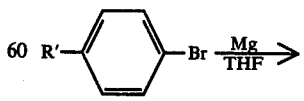

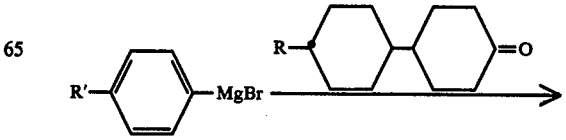

-continued

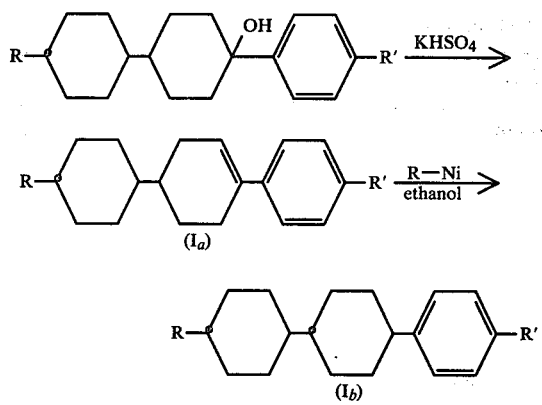

(In the above equations, R and R' are the same groups as defined above.)

The process for preparing compounds of the present invention and the use examples thereof will be further described in detail by way of Examples.

EXAMPLE 1

Preparation of 4-methoxy-[4'-(trans-4''-propylcyclohexyl)cyclohexen-1'-yl]benzene A magnesium slice (1.2 g, 0.049 mol) was placed in a three-neck flask, and 30 ml of a solution of 4-bromoanisole (9.2 g, 0.049 mol) dissolved in tetrahydrofuran was slowly dropwise added with stirring in nitrogen gas current while the reaction temperature was maintained at 30°–35° C. As a result of the reaction, magnesium dissolved in 3 hours to form a uniform solution containing 4-methoxyphenylmagnesium bromide, to which 50 ml of a solution of 4-(trans-4'-propylcyclohexyl)cyclohexanone (10.9 g, 0.049 mol) dissolved in tetrahydrofuran was dropwise added as rapidly as possible while the reaction temperature was maintained at 5°–10° C. After the dropwise addition, the mixture was heated up to 35° C. and agitated for 30 minutes, followed by adding 50 ml of 3 N hydrochloric acid. The reaction liquid was then taken into a separating funnel and subjected to extraction three times with toluene, followed by washing combined toluene layers with water till it became neutral and then distilling off toluene under reduced pressure to give as residue, 4-methoxy-[1'-hydroxy-4'-(trans-4''-propylcyclohexyl)-cyclohexyl]benzene.

Potassium hydrogen sulfate (6 g) was added to it and the mixture was subjected to dehydration in nitrogen gas current at 160° C. for 2 hours. After cooling, toluene (200 ml) was added and potassium hydrogen sulfate was filtered off, followed by washing the resulting toluene layer with water till the washing water became neutral. Toluene was then distilled off under reduced pressure to give an oily substance as residue which was recrystallized from ethanol to give objective 4-methoxy-[4'-(trans-4''-propylcyclohexyl)cyclohexene-1'-yl]benzene. This compound had a crystalline-smectic (C-Sm)point of 95.2° C., a smectic-nematic (Sm-N) point of 139.2° C. and a nematic-transparent (N-I)point of 207.4° C. Yield: 7.0 g (46%). The fact that this product was an objective compound was confirmed by NMR spectra, IR absorption spectra and elementary analysis.

EXAMPLES 2–61

Example 1 was repeated except that the carbon numbers of R and R' in the above formula ($I_a$) were varied. The yields (g and %) and physical properties of the resulting compounds are shown in Table 1 together with those in Example 1.

TABLE 1

Compound of R—⬡—⬡—⬡—R' (formula ($I_a$))

| Example | R | R' | Amount of raw material 4-substituted hexanone used (g) | Yield (g) | Yield (%) | C-Sm point or C-I point | Sm-N point | N-I point or Sm-I point |
|---|---|---|---|---|---|---|---|---|
| 1 | $C_3H_7$ | $CH_3O$ | 8.7 | 7.0 | 46 | 93.2 | 139.2 | 207.4 |
| 2 | $C_3H_7$ | $C_3H_7O$ | 8.7 | 8.1 | 49 | 87.4 | 187.9 | 200.5 |
| 3 | $C_3H_7$ | $C_7H_{15}O$ | 9.6 | 8.0 | 41 | 70.1 | — | 193.6 |
| 4 | $C_4H_9$ | $C_2H_5O$ | 9.2 | 5.1 | 31 | 81.8 | 182.6 | 202.2 |
| 5 | $C_4H_9$ | $C_6H_{13}O$ | 9.2 | 5.0 | 26 | 72.6 | — | 199.2 |
| 6 | $C_5H_{11}$ | $C_3H_7O$ | 9.8 | 5.2 | 29 | 81.0 | — | 196.8 |
| 7 | $C_6H_{13}$ | $CH_3O$ | 13.0 | 5.5 | 30 | 66.0 | 133.1 | 180.0 |
| 8 | $C_6H_{13}$ | $CH_3$ | 10.3 | 3.0 | 18 | 66.1 | 144.1 | 170.2 |
| 9 | $C_7H_{15}$ | $C_3H_7O$ | 10.9 | 15.4 | 79 | 79.3 | — | 195.9 |
| 10 | $C_7H_{15}$ | $C_7H_{15}O$ | 1.0 | 0.9 | 55 | 79.6 | — | 192.0 |
| 11 | H | H | 7.7 | 5.5 | 43 | 97.7 ~98.4 | — | — |
| 12 | $C_3H_7$ | H | 26.2 | 19.4 | 48 | 68.6 | 77.1 | 105.5 |
| 13 | $C_4H_9$ | H | 9.2 | 4.7 | 32 | 75.8 | 89.0 | 104.8 |
| 14 | $C_5H_{11}$ | H | 29.5 | 19.5 | 42 | 69.8 | 83.9 | 111.8 |
| 15 | H | $CH_3O$ | 21.3 | 16 | 50 | 115.0 ~116.0 | — | — |
| 16 | H | $C_2H_5O$ | 21.3 | 20 | 60 | 109.8 | — | 119.1 |
| 17 | H | $C_3H_7O$ | 21.3 | 10 | 29 | 100.3 | — | 118.0 |
| 18 | H | $C_4H_9O$ | 21.3 | 19 | 52 | 73.5 | — | 112.1 |
| 19 | H | $C_5H_{11}O$ | 21.3 | 22 | 58 | 73.5 | — | 108.6 |
| 20 | $C_2H_5$ | $CH_3$ | 8.3 | 4.2 | 40 | 74.8 | 130.2 | 151.5 |

TABLE 1-continued

Compound of R—⬡—⬡—⌬—R' (formula (I$_a$))

| Example | R | R' | Amount of raw material 4-substituted hexanone used (g) | Yield (g) | Yield (%) | C-Sm point or C-I point | Sm-N point | N-I point or Sm-I point |
|---|---|---|---|---|---|---|---|---|
| 21 | $C_2H_5$ | $C_2H_5$ | 8.3 | 1.6 | 15 | room temp. or lower | — | 155.9 |
| 22 | $C_2H_5$ | $C_3H_7$ | 8.3 | 1.8 | 15 | room temp. or lower | — | 156.2 |
| 23 | $C_2H_5$ | $C_5H_{11}$ | 8.3 | 1.5 | 8 | room temp. or lower | — | 153.7 |
| 24 | $C_2H_5$ | $C_6H_{13}$ | 8.3 | 2.2 | 15 | room temp. or lower | — | 150.6 |
| 25 | $C_3H_7$ | $CH_3$ | 8.9 | 3.0 | 25 | 80.5 | 133.3 | 180.8 |
| 26 | $C_3H_7$ | $C_3H_7$ | 8.9 | 6.0 | 45 | 57.0 | — | 163.7 |
| 27 | $C_3H_7$ | $C_4H_9$ | 8.9 | 3.0 | 22 | room temp. or lower | — | 176.3 |
| 28 | $C_3H_7$ | $C_5H_{11}$ | 8.9 | 2.7 | 19 | room temp. or lower | — | 175.0 |
| 29 | $C_3H_7$ | $C_6H_{13}$ | 8.9 | 1.1 | 8 | room temp. or lower | — | 173.4 |
| 30 | $C_3H_7$ | $C_2H_5O$ | 13.3 | 9.5 | 29 | 80.0 | 170.0 | 208.5 |
| 31 | $C_3H_7$ | $C_4H_9O$ | 8.7 | 1.6 | 12 | 60.2 | — | 195.6 |
| 32 | $C_3H_7$ | $C_5H_{11}O$ | 6.4 | 2.2 | 21 | 75.8 | 181.0 | 197.2 |
| 33 | $C_3H_7$ | $C_6H_{13}O$ | 10.1 | 4.4 | 25 | 71.3 | — | 192.7 |
| 34 | $C_5H_{11}$ | $CH_3$ | 10.0 | 4.4 | 34 | 70.4 | 141.8 | 174.4 |
| 35 | $C_5H_{11}$ | $C_3H_7$ | 10.0 | 6.7 | 48 | 54.6 | 172.3 | 175.6 |
| 36 | $C_5H_{11}$ | $C_4H_9$ | 10.0 | 1.0 | 7 | room temp. or lower | — | 182.0 |
| 37 | $C_5H_{11}$ | $C_5H_{11}$ | 10.0 | 6.1 | 40 | room temp. or lower | — | 181.0 |
| 38 | $C_5H_{11}$ | $C_6H_{13}$ | 10.0 | 7.3 | 45 | room temp. or lower | — | 182.0 |
| 39 | $C_5H_{11}$ | $CH_3O$ | 9.8 | 2.5 | 15 | 83.0 | 148.8 | 199.6 |
| 40 | $C_5H_{11}$ | $C_2H_5O$ | 7.3 | 3.0 | 29 | 84.9 | 189.4 | 204.0 |
| 41 | $C_5H_{11}$ | $C_4H_9O$ | 9.8 | 5.6 | 38 | 65.5 | — | 208.3 |
| 42 | $C_5H_{11}$ | $C_5H_{11}O$ | 7.3 | 1.8 | 12 | 75.8 | — | 206.0 |
| 43 | $C_5H_{11}$ | $C_6H_{13}O$ | 7.4 | 7.2 | 62 | 73.6 | — | 203.3 |
| 44 | $C_5H_{11}$ | $C_7H_{15}O$ | 11.4 | 7.4 | 38 | 83.7 | — | 196.8 |
| 45 | $C_7H_{15}$ | $CH_3O$ | 7.5 | 8.0 | 60 | 81.1 | 147.3 | 182.0 |
| 46 | $C_2H_5$ | $C_4H_9$ | 8.3 | 3.5 | 27 | room temp. or lower | — | 150.7 |
| 47 | $C_2H_5$ | $C_7H_{15}$ | 8.3 | 1.0 | 7 | room temp. or lower | — | 139.6 |
| 48 | $C_2H_5$ | $C_8H_{17}$ | 8.3 | 4.4 | 30 | room temp. or lower | — | 148.4 |
| 49 | $C_3H_7$ | $C_7H_{15}$ | 8.9 | 2.8 | 19 | room temp. or lower | — | 165.9 |
| 50 | $C_4H_9$ | $CH_3$ | 9.5 | 6.3 | 51 | 76.7 | 130.1 | 170.4 |
| 51 | $C_4H_9$ | $C_2H_5$ | 9.5 | 4.5 | 35 | 37.3 | — | 163.9 |
| 52 | $C_4H_9$ | $C_3H_7$ | 9.5 | 1.6 | 12 | room temp. or lower | — | 181.6 |
| 53 | $C_4H_9$ | $C_5H_{11}$ | 9.5 | 2.6 | 18 | room temp. or lower | — | 181.8 |
| 54 | $C_5H_{11}$ | $C_7H_{15}$ | 10.0 | 2.0 | 12 | room temp. or lower | — | 174.5 |

TABLE 1-continued

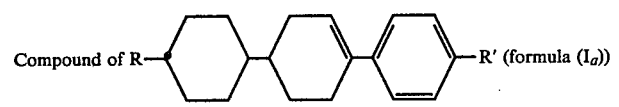

Compound of R—⬡—⬡—⌬—R' (formula (I_a))

| Example | R | R' | Amount of raw material 4-substituted hexanone used (g) | Yield (g) | Yield (%) | C-Sm point or C-I point | Sm-N point | N-I point or Sm-I point |
|---|---|---|---|---|---|---|---|---|
| 55 | $C_7H_{15}$ | $CH_3$ | 11.1 | 2.5 | 18 | 67.4 | 147.9 | 174.6 |
| 56 | $C_7H_{15}$ | $C_2H_5$ | 11.1 | 8.2 | 56 | 42.6 | 163.3 | 165.5 |
| 57 | $C_7H_{15}$ | $C_3H_7$ | 11.1 | 9.0 | 59 | 40.8 | — | 171.8 |
| 58 | $C_7H_{15}$ | $C_4H_9$ | 11.1 | 11:6 | 74 | room temp. or lower | — | 179.3 |
| 59 | $C_7H_{15}$ | $C_5H_{11}$ | 11.1 | 10.0 | 61 | room temp. or lower | — | 182.0 |
| 60 | $C_7H_{15}$ | $C_6H_{13}$ | 11.1 | 9.0 | 53 | room temp. or lower | — | 179.8 |
| 61 | $C_7H_{15}$ | $C_7H_{15}$ | 11.1 | 5.1 | 29 | 49.9 | — | 179.4 |

EXAMPLE 62

Preparation of 4-methoxy-[trans-4'-(trans-4''-propylcyclohexyl)cyclohexyl]benzene 4-Methoxy-[4'-(trans-4''-propylcyclohexyl)cyclohexen-1'-yl]benzene (7.0 g) prepared in Example 1 was dissolved in ethanol (120 ml) and Raney nickel catalyst (1.0 g) was added, followed by catalytic reduction at 50° C. under the atmospheric pressure (the quantity of hydrogen absorbed: 500 ml). After filtering off the catalyst, the solution was subjected to recrystallization as it was. Since the resulting material was a mixture of cis-form with trans-form, it was further repeatedly recrystallized from ethanol to isolate the trans-form. This compound was 4-methoxy-[trans-4'-(trans-4''-propylcyclohexyl)cyclohexyl]benzene, and had a crystalline-smectic (C-Sm) point of 79.2° C., a smectic-nematic (Sm-N) point of 128.4° C. and a nematic-transparent (N-I) point of 211.5° C. Yield: 2.8 g (40%). The fact that this product was an objective compound was confirmed by NMR spectra and elementary analysis.

EXAMPLES 63-108

Example 62 was repeated except that the carbon numbers of the alkyl group and the alkoxy group were varied. The yields and physical properties of the resulting compounds are shown in Table 2 together with those in Example 62.

TABLE 2

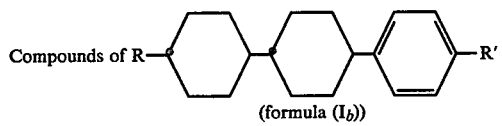

Compounds of R—⬡—⬡—⌬—R' (formula (I_b))

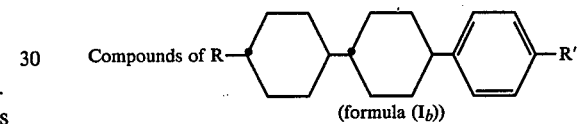

| Example | R | R' | Yield (%) | C-Sm point or C-I point | Sm-N point | N-I point or Sm-I point |
|---|---|---|---|---|---|---|
| 62 | $C_3H_7$ | $CH_3O$ | 40 | 79.2 | 128.4 | 211.5 |
| 63 | $C_3H_7$ | $C_3H_7O$ | 24 | 81.6 | 179.5 | 201.4 |
| 64 | $C_3H_7$ | $C_7H_{15}O$ | 40 | 72.1 | 172.0 | 178.0 |
| 65 | $C_4H_9$ | $C_2H_5O$ | 30 | 84.7 | 172.5 | 211.5 |
| 66 | $C_4H_9$ | $C_6H_{13}O$ | 19 | 70.0 | — | 186.3 |
| 67 | $C_5H_{11}$ | $C_3H_7O$ | 38 | 56.3 | 195.1 | 201.8 |
| 68 | $C_6H_{13}$ | $CH_3O$ | 22 | 70.5 | 154.5 | 196.5 |
| 69 | $C_6H_{13}$ | $CH_3$ | 12 | 135.8 | 142.5 | 167.8 |
| 70 | $C_7H_{15}$ | $C_3H_7O$ | 32 | 62.7 | — | 194.6 |
| 71 | $C_7H_{15}$ | $C_7H_{15}O$ | 20 | 58.1 | — | 188.0 |
| 72 | $C_3H_7$ | H | 23 | 75.9 | 91.8 | 100.4 |
| 73 | $C_4H_9$ | H | 35 | 70.1 | — | 109.2 |
| 74 | $C_5H_{11}$ | H | 15 | 61.6 | 107.9 | 111.8 |
| 75 | H | $CH_3O$ | 31 | 92.8 | — | — |
| 76 | H | $C_2H_5O$ | 25 | 87.0 | — | 98.7 |
| 77 | H | $C_3H_7O$ | 30 | 90.4 | — | 113.0 |
| 78 | H | $C_4H_9O$ | 20 | 85.3 | — | 101.0 |
| 79 | H | $C_5H_{11}O$ | 20 | 62.4 | — | 87.2 |
| 80 | $C_3H_7$ | $CH_3$ | 20 | 64.6 | 109.7 | 179.8 |
| 81 | $C_3H_7$ | $C_2H_5$ | 13 | 31.0 | 161.3 | 162.7 |
| 82 | $C_3H_7$ | $C_3H_7$ | 20 | room temp. or lower | — | 177.5 |
| 83 | $C_3H_7$ | $C_2H_5O$ | 5 | 84.6 | 149.1 | 210.1 |
| 84 | $C_3H_7$ | $C_4H_9O$ | 38 | 65.3 | 179.1 | 190.9 |
| 85 | $C_3H_7$ | $C_5H_{11}O$ | 21 | 60.8 | 175.8 | 185.6 |
| 86 | $C_3H_7$ | $C_6H_{13}O$ | 27 | 77.0 | 175.3 | 185.3 |
| 87 | $C_4H_9$ | $CH_3$ | 33 | 58.0 | 135.2 | 173.9 |
| 88 | $C_5H_{11}$ | $CH_3$ | 39 | 55.8 | 138.0 | 178.6 |
| 89 | $C_5H_{11}$ | $C_2H_5$ | 26 | 37.8 | — | 173.2 |
| 90 | $C_5H_{11}$ | $C_3H_7$ | 16 | 48.6 | — | 181.0 |
| 91 | $C_5H_{11}$ | $C_4H_9$ | 18 | room temp. or lower | — | 190.6 |
| 92 | $C_5H_{11}$ | $CH_3O$ | 30 | 66.3 | 150.1 | 207.7 |
| 93 | $C_5H_{11}$ | $C_2H_5O$ | 27 | 81.8 | 176.3 | 215.2 |
| 94 | $C_5H_{11}$ | $C_4H_9O$ | 7 | 63.2 | 199.2 | 200.6 |
| 95 | $C_5H_{11}$ | $C_5H_{11}O$ | 16 | 61.4 | — | 196.7 |
| 96 | $C_5H_{11}$ | $C_6H_{13}O$ | 10 | 58.1 | — | 192.5 |
| 97 | $C_7H_{15}$ | $CH_3O$ | 22 | 68.8 | 153.0 | 194.7 |
| 98 | $C_2H_5$ | $CH_3$ | 10 | 62.8 | 103.7 | 142.3 |
| 99 | $C_2H_5$ | $C_2H_5$ | 6 | 55.1 | — | 151.9 |

TABLE 2-continued

Compounds of R—⬡—⬡—⌬—R'

(formula (I$_b$))

| Example | R | R' | Yield (%) | C-Sm point or C-I point | Sm-N point | N-I point or Sm-I point |
|---|---|---|---|---|---|---|
| 100 | C$_2$H$_5$ | C$_3$H$_7$ | 9 | room temp. or lower | — | 160.8 |
| 101 | C$_2$H$_5$ | C$_4$H$_9$ | 23 | room temp. or lower | — | 158.6 |
| 102 | C$_2$H$_5$ | C$_5$H$_{11}$ | 17 | room temp. or lower | — | 151.0 |
| 103 | C$_2$H$_5$ | C$_6$H$_{13}$ | 21 | room temp. or lower | — | 148.6 |
| 104 | C$_3$H$_7$ | C$_4$H$_9$ | 31 | room temp. or lower | — | 189.6 |
| 105 | C$_3$H$_7$ | C$_5$H$_{11}$ | 19 | room temp. or lower | — | 172.2 |
| 106 | C$_3$H$_7$ | C$_6$H$_{13}$ | 10 | room temp. or lower | — | 171.0 |
| 107 | C$_5$H$_{11}$ | C$_5$H$_{11}$ | 11 | room temp. or lower | — | 189.8 |
| 108 | C$_5$H$_{11}$ | C$_6$H$_{13}$ | 7 | room temp. or lower | — | 185.9 |

Next, use examples will be described. Parts referred to herein are by weight.

EXAMPLE 109 (USE EXAMPLE 1)

A liquid crystal composition (A) consisting of
trans-4-propyl-(4'-cyanophenyl)cyclohexane (28%),
trans-4-pentyl-(4'-cyanophenyl)cyclohexane (43%), and
trans-4-heptyl-(4'-cyanophenyl)cyclohexane (29%),
has a nematic temperature range of $-3°-+52°$ C., a dielectric anisotropy value $\Delta\epsilon$ of $+10.5$, a threshold voltage of 1.53 V and a saturation voltage of 2.12 V. Also it has a viscosity of 23 cp at 20° C.

To this liquid crystal composition A (80 parts) were added 4-methoxy-[4'-(trans-4''-propylcyclohexyl)cyclohexen-1'-yl]benzene (10 parts) prepared in Example 1 and 4-ethoxy-[4'-(trans-4''-butylcyclohexyl)cyclohexen-1'-yl]benzene (10 parts) prepared in Example 4 to give a liquid crystal mixture. This mixture had as greatly extended a nematic temperature range as $-10°-+81.0°$ C. Its $\Delta\epsilon$ was reduced down to 8.8 and its threshold voltage and saturation voltage were elevated up to 1.63 V and 2.28 V, respectively and nevertheless its viscosity (23 cp) was unchanged.

EXAMPLE 110 (USE EXAMPLE 2)

To the above liquid crystal composition (A) (90 parts) was added 4'-(trans-4''-pentylcyclohexyl)cyclohexen-1'-yl-benzene (10 parts) prepared in Example 14 to give a liquid crystal mixture. This mixture had as extended a nematic temperature range as $-5°-+58°$ C. Its $\Delta\epsilon$, threshold voltage and saturation voltage were elevated up to $+9.0$, 1.60 V and 2.30 V, respectively, but its viscosity (23 cp) was unchanged.

EXAMPLE 111 (USE EXAMPLE 3)

To the liquid crystal composition (A) (80 parts) were added 4-methoxy-[trans-4'-(trans-4''-propylcyclohexyl)cyclohexyl]benzene (10 parts) prepared in Example 62 and 4-methoxy-[trans-4'-(trans-4''-hexylcyclohexyl)cyclohexyl]benzene (10 parts) prepared in Example 68 to give a liquid crystal mixture. This mixture had as extended a nematic temperature range as $-10°-+78°$ C. Its $\Delta\epsilon$ was reduced down to $+8.8$ and its threshold voltage and saturation voltage were elevated up to 1.63 V and 2.28 V, respectively, but its viscosity (23 cp) was unchanged. Thus it is seen that the compounds of the present invention are effective for lower temperature actuation.

EXAMPLE 112 (USE EXAMPLE 4)

To the liquid crystal composition (A) (60 parts) were added [trans-4'-(trans-4''-propylcyclohexyl)cyclohexyl]benzene (20 parts) prepared in Example 72 and [trans-4'-(trans-4''-pentylcyclohexyl)cyclohexyl]benzene (20 parts) prepared in Example 74 to give a liquid crystal mixture. This mixture had as extended a nematic temperature range as $-5°-+73°$ C. Its $\Delta\epsilon$ was reduced down to $+7.2$ and its threshold voltage and saturation voltage were somewhat elevated up to 1.75 V and 2.30 V, respectively, but its viscosity (23 cp) was unchanged. Thus, by adding the compounds of the present invention, it was possible to extend the nematic temperature range with slight increases in the threshold voltage and saturation voltage in spite of reduction in the dielectric anisotropy value.

EXAMPLE 113 (USE EXAMPLE 5)

A liquid crystal composition consisting of
4-pentyl-4'-cyanobiphenyl (45%),
4-heptyl-4'-cyanobiphenyl (29%),
4-octyloxy-4'-cyanobiphenyl (15%) and
4-pentyl-4'-cyanoterphenyl (11%),
had a N-I point of 63.3° C. and a viscosity of 48 cp at 20° C.

To this composition (95 parts) was added 1-(trans-4'-cyclohexylcyclohexyl)-4-propoxybenzene (5 parts) prepared in Example 77 to give a liquid crystal mixture having a N-I point of 61.8° C. and a viscosity of 47.5 cp at 20° C.

EXAMPLE 114 (USE EXAMPLE 6)

A composition consisting of
4-pentyl-4'-cyanobiphenyl (51%),
4-heptyl-4'-cyanobiphenyl (32%) and
4-octyloxy-4'-cyanobiphenyl (17%),
had a N-I point of 44.3° C. and a viscosity of 40 cp at 20° C.

To this composition (90 parts) was added 1-(trans-4'-cyclohexylcyclohexyl)-4-methoxybenzene (10 parts) prepared in Example 75 to give a liquid crystal mixture having a N-I point of 44.1° C. and a viscosity of 39 cp at 20° C.

What is claimed is:

1. A benzene derivative expressed by the formula

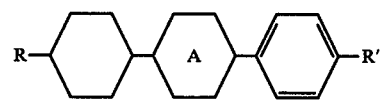

wherein R represents a hydrogen atom or an alkyl group of 1 to 10 carbon atoms; R' represents a hydrogen atom, an alkyl group of 1 to 10 carbon atoms or an alkoxy group of 1 to 10 carbon atoms;

represents 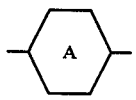

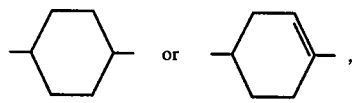

and wherein either one of R or R' must be an alkyl or alkoxy group.

2. A 4-Substituted or unsubstituted-[trans-4'-(trans-4''-alkylcyclohexyl)cyclohexyl]benzene expressed by the formula

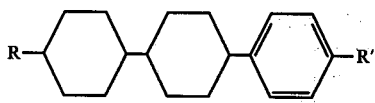

wherein R represents a hydrogen atom or an alkyl group of 1 to 10 carbon atoms; R' represents a hydrogen atom, an alkyl group of 1 to 10 carbon atoms or an alkoxy group of 1 to 10 carbon atoms, and wherein either one of R or R' must be an alkyl or alkoxy group.

3. A 4-Substituted or unsubstituted-[4'-(trans-4''-alkylcyclohexyl)cyclohexen-1'-yl]benzene expressed by the formula

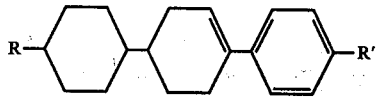

wherein R represents a hydrogen atom or an alkyl group of 1 to 10 carbon atoms; R' represents a hydrogen atom, an alkyl group of 1 to 10 carbon atoms or an alkoxy group of 1 to 10 carbon atoms, and wherein either one of R or R' must be an alkyl or alkoxy group.

4. A liquid crystal composition comprising a mixture of compounds at least one of which is a compound as claimed in claim 1.

5. In a liquid crystal display cell using a liquid crystal composition, the improvement which comprises a mixture of compounds at least one of which is a compound as claimed in claim 1.

* * * * *

UNITED STATES PATENT AND TRADEMARK OFFICE
CERTIFICATE OF CORRECTION

PATENT NO. : 4,422,951
DATED : December 27, 1983
INVENTOR(S) : SHIGERU SUGIMORI ET AL.

It is certified that error appears in the above—identified patent and that said Letters Patent is hereby corrected as shown below:

On the title page;
Line [75] Inventors:

Change "Shigeru Sugimori, Fujisawashi; Tetsukiho Kojima; Masakazu Tsuji, both of Yokohamashi, all of Japan"

to -- Shigeru Sugimori, Fujisawashi; Tetsuhiko Kojima, Masakazu Tsuji, both of Yokohamashi, all of Japan --.

Signed and Sealed this

Thirtieth Day of July 1985

[SEAL]

Attest:

DONALD J. QUIGG

*Attesting Officer*  *Acting Commissioner of Patents and Trademarks*